(12) United States Patent
Dorsel

(10) Patent No.: US 6,825,929 B2
(45) Date of Patent: Nov. 30, 2004

(54) SIMULTANEOUSLY READING DIFFERENT REGIONS OF A CHEMICAL ARRAY

(75) Inventor: Andreas N. Dorsel, Menlo Park, CA (US)

(73) Assignee: Agilent Technologies, Inc., Palo Alto, CA (US)

(*) Notice: Subject to any disclaimer, the term of this patent is extended or adjusted under 35 U.S.C. 154(b) by 214 days.

(21) Appl. No.: 10/261,807

(22) Filed: Sep. 30, 2002

(65) Prior Publication Data

US 2004/0061071 A1 Apr. 1, 2004

(51) Int. Cl.$^7$ .............................................. G01N 21/64
(52) U.S. Cl. ................ 356/318; 250/458.1; 422/82.08; 435/6; 436/172
(58) Field of Search ............................. 356/317, 318, 356/417; 250/458.1, 459.1, 461.1, 461.2; 422/82.08; 435/6; 436/172

(56) References Cited

U.S. PATENT DOCUMENTS

| | | | |
|---|---|---|---|
| 6,171,793 B1 | 1/2001 | Phillips et al. | |
| 6,320,196 B1 | 11/2001 | Dorsel et al. | |
| 6,329,661 B1 | 12/2001 | Perov et al. | |
| 6,355,921 B1 | 3/2002 | Staton et al. | |
| 6,371,370 B2 | 4/2002 | Sadler et al. | |
| 2003/0087282 A1 * | 5/2003 | Oshida et al. | ................ 435/6 |

* cited by examiner

Primary Examiner—F. L. Evans
(74) Attorney, Agent, or Firm—Gordon M. Stewart

(57) ABSTRACT

A method of interrogating an addressable array having a plurality of different chemical features. The method may include simultaneously illuminating different regions of the array with light of different intensities (which, for example, can, but need not be, also of a same waveband). Light emitted from the different regions in response to the illuminating (which light, for example, can, but need not be, of a same waveband) may be simultaneously detected with different detectors. An apparatus, addressable array unit, and related methods are further provided.

28 Claims, 3 Drawing Sheets

SIMULTANEOUSLY READING DIFFERENT REGIONS OF A CHEMICAL ARRAY

FIELD OF THE INVENTION

This invention relates to arrays, particularly biopolymer arrays such as DNA or protein arrays, which are useful in diagnostic, screening, gene expression analysis, and other applications.

BACKGROUND OF THE INVENTION

For the purposes of the discussion below, cited art is not admitted to constitute prior art to the present application.

Polynucleotide arrays (such as DNA or RNA arrays) and peptide arrays, are known and may be used, for example, as diagnostic or screening tools. Such arrays include regions (sometimes referenced as spots or features) of usually different sequence polynucleotides or peptides arranged in a predetermined configuration on a substrate. The array is "addressable" in that different features have different predetermined locations ("addresses") on a substrate carrying the array.

Biopolymer arrays can be fabricated using in situ synthesis methods or deposition of the previously obtained biopolymers. The in situ fabrication methods include those described in U.S. Pat. No. 5,449,754 for synthesizing peptide arrays, and in U.S. Pat. No. 6,180,351 and WO 98/41531 and the references cited therein for polynucleotides. In situ methods also include photolithographic techniques such as described, for example, in WO 91/07087, WO 92/10587, WO 92/10588, and U.S. Pat. No. 5,143,854. The deposition methods basically involve depositing biopolymers at predetermined locations on a substrate which are suitably activated such that the biopolymers can link thereto. Biopolymers of different sequence may be deposited at different feature locations on the substrate to yield the completed array. Procedures known in the art for deposition of biopolymers, particularly DNA such as whole oligomers or cDNA, are described, for example, in U.S. Pat. No. 5,807,522 (touching drop dispensers to a substrate), and in PCT publications WO 95/25116 and WO 98/41531, and elsewhere (use of a pulse jet in the form of a piezoelectric inkjet head).

Further details of large scale fabrication of biopolymer arrays by depositing either previously obtained biopolymers or by the in situ method, are disclosed in U.S. Pat. Nos. 6,242,266, 6,232,072, 6,180,351, and U.S. Pat. No. 6,171,797.

In array fabrication, the quantities of DNA available for the array are usually very small and expensive. Sample quantities available for testing are usually also very small and it is therefore desirable to simultaneously test the same sample against a large number of different probes on an array. These conditions require the manufacture and use of arrays with large numbers of very small, closely spaced features.

The arrays, when exposed to a sample, will exhibit a binding pattern. The array can be read by observing this binding pattern by, for example, labeling all targets such as polynucleotide targets (for example, DNA), in the sample with a suitable label (such as a fluorescent compound), scanning an illuminating beam across the array and accurately detecting the fluorescent signal from the different features of the array. Assuming that the different sequence polynucleotides were correctly deposited in accordance with the predetermined configuration, then the observed binding pattern will be indicative of the presence and/or concentration of one or more polynucleotide components in the sample. Peptide or arrays of other chemical moieties can be used in a similar manner.

Techniques and apparatus for scanning chemical arrays are described, for example, in U.S. Pat. Nos. 6,406,849, 6,371,370, 6,355,921, 5,763,870 and U.S. Pat. No. 5,945,679. Apparatus which reads an array by scanning an illuminating beam by the foregoing technique are often referred to as scanners and the technique itself often referred to as scanning. Conventionally, such scanning has been done by illuminating array features on a front surface of the substrate one pixel at a time.

Array scanners typically use one or more laser beams of different waveband as light sources, which are scanned over pixels covering the array features. The lasers are generally set to provide as much light as possible to a scanned array, and consequently the relative intensities of such different waveband light sources are close to equal, or about 2/1 or less. detectors (typically fluorescence detectors) each with a very high light sensitivity is normally desirable to achieve maximum signal-to-noise in detecting hybridized molecules, particularly in array scanners used for DNA sequencing or gene expression studies. At present, photomultiplier tubes ("PMTs") are still the detector of choice although charge coupled devices ("CCDs") and avalanche photodiodes ("APDs") can also be used. PMTs and APDs are typically used for temporally sequential scanning of array features, while CCDs permit scanning many features in parallel (for example, one line of features simultaneously, in which case an illuminating line may be used).

A difficulty in reading chemical arrays is that given the large numbers of features which may be present, for example, many thousands of features, and given the various samples that may be exposed to the array, the fluorescent signals detected from different features can vary over a wide range of intensities. In order to obtain the maximum signal from a feature it is desirable to illuminate the array features with light of an intensity and for a time, as high as possible so as to obtain a detectable signal even from features which may only have a few labels present. On the other hand though, in this situation a detected signal from a feature having many labels may be so strong as to cause detector saturation (that is, further increases in signal from the array feature no longer cause an increase in detector signal output). In this event, meaningful measurements from such features are lost. The range over which meaningful signals may be obtained from a feature by an array reader may be referenced as its dynamic range.

It would be desirable then, to provide an array reader with a high dynamic range covering both features which may produce a low or high detectable signal, and which is not overly complex to construct.

SUMMARY OF THE INVENTION

The present invention provides a method of interrogating an addressable array having a plurality of different chemical features. The method may include simultaneously illuminating different regions of the array with light of different intensities (which, for example can, but need not be, of a same waveband). Light emitted from the different regions in response to the illuminating (which light can, but need not be, of a same waveband) may be simultaneously detected with different detectors.

The present invention further provides an apparatus which includes a light system to provide the simultaneous illumination to the different regions of the array, and different light detectors for the simultaneous detection from the different regions, both as mentioned above.

The present invention further provides an addressable array unit. The addressable array unit may have a plurality of different chemical features (such as different polynucleotide or poly-amino acid features). The array unit may also include instructions that different regions of the array can be simultaneously illuminated with light of different intensities and that light emitted from the different regions in response to the illuminating can be simultaneously detected from those regions with different detectors. The instructions may further include an indication of the relative light intensities for the simultaneously illuminated regions or detector sensitivities for the simultaneously detected regions. Alternatively, rather than the array unit including any instructions, it may instead include a code (for example, a machine readable code) linked to such instructions or a combination of part of the instructions and a code linked to the remainder. Such a code can, for example, be located on a substrate carrying the array or an element which carries the substrate.

The present invention also provides a method for receiving a code as already described, and communicating the instructions in response to the received code.

The present invention may provide one or more of the following or other benefits. For example, a high dynamic range may be obtained without a need for scanning the array multiple times.

BRIEF DESCRIPTION OF THE DRAWINGS

Embodiments of the invention will now be described with reference to the drawings, in which.

To facilitate understanding, the same reference numerals have been used, where practical, to designate similar elements that are common to the FIGS.

DETAILED DESCRIPTION OF THE INVENTION

Figure 1:
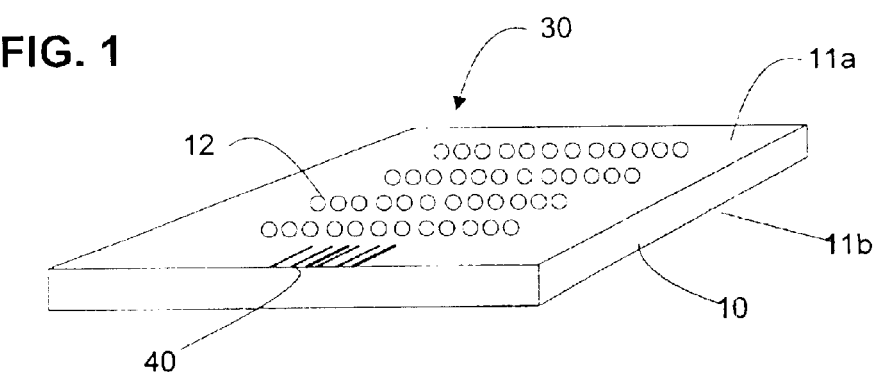
FIG. 1 is a perspective view of an array unit of the present invention.

In the present application, unless a contrary intention appears, the following terms refer to the indicated characteristics. A "biopolymer" is a polymer of one or more types of repeating units. Biopolymers are typically found in biological systems and particularly include polysaccharides (such as carbohydrates), and peptides (which term is used to include polypeptides and proteins) and polynucleotides as well as their analogs such as those compounds composed of or containing amino acid analogs or non-amino acid groups, or nucleotide analogs or non-nucleotide groups. This includes polynucleotides in which the conventional backbone has been replaced with a non-naturally occurring or synthetic backbone, and nucleic acids (or synthetic or naturally occurring analogs) in which one or more of the conventional bases has been replaced with a group (natural or synthetic) capable of participating in Watson-Crick type hydrogen bonding interactions. Polynucleotides include single or multiple stranded configurations, where one or more of the strands may or may not be completely aligned with another. A "nucleotide" refers to a sub-unit of a nucleic acid and has a phosphate group, a 5 carbon sugar and a nitrogen containing base, as well as functional analogs (whether synthetic or naturally occurring) of such sub-units which in the polymer form (as a polynucleotide) can hybridize with naturally occurring polynucleotides in a sequence specific manner analogous to that of two naturally occurring polynucleotides. For example, a "biopolymer" includes DNA (including cDNA), RNA, oligonucleotides, and PNA and other polynucleotides as described in U.S. Pat. No. 5,948,902 and references cited therein (all of which are incorporated herein by reference), regardless of the source. An "oligonucleotide" generally refers to a nucleotide multimer of about 10 to 100 nucleotides in length, while a "polynucleotide" includes a nucleotide multimer having any number of nucleotides. A "biomonomer" references a single unit, which can be linked with the same or other biomonomers to form a biopolymer (for example, a single amino acid or nucleotide with two linking groups one or both of which may have removable protecting groups). A biomonomer fluid or biopolymer fluid reference a liquid containing either a biomonomer or biopolymer, respectively (typically in solution).

An "array", unless a contrary intention appears, includes any one-, two- or three-dimensional arrangement of addressable regions bearing a particular chemical moiety or moieties (for example, biopolymers such as polynucleotide sequences) associated with those regions. An array is "addressable" in that it has multiple regions of different moieties (for example, different polynucleotide sequences) such that a region (also referenced as a "feature" or "spot" of the array) at a particular predetermined location (an "address") on the array will detect a particular target or class of targets (although a feature may incidentally detect non-targets of that feature). Note that the finite small areas on the array which can be illuminated and from which any resulting emitted light can be simultaneously (or shortly thereafter) detected, define pixels which are typically substantially smaller than a feature (typically having an area about $\frac{1}{10}$ to $\frac{1}{100}$ the area of a feature). Array features are typically, but need not be, separated by intervening spaces. In the case of an array, the "target" will be referenced as a moiety in a mobile phase (typically fluid), to be detected by probes ("target probes") which are bound to the substrate at the various features. However, either of the "target" or "target probes" may be the one which is to be evaluated by the other (thus, either one could be an unknown mixture of polynucleotides to be evaluated by binding with the other). An "array layout" refers to one or more characteristics of the features, such as feature positioning on the substrate, one or more feature dimensions, and an indication of a moiety at a given location. The array "substrate" includes everything of the array unit behind the substrate front surface. "Hybridizing" and "binding", with respect to polynucleotides, are used interchangeably.

When one item is indicated as being "remote" from another, this is referenced that the two items are at least in different buildings, and may be at least one mile, ten miles, or at least one hundred miles apart. "Communicating" information references transmitting the data representing that information as electrical signals over a suitable communication channel (for example, a private or public network). "Forwarding" an item refers to any means of getting that item from one location to the next, whether by physically transporting that item or otherwise (where that is possible) and includes, at least in the case of data, physically transporting a medium carrying the data or communicating the data. An array "unit" may be the array plus only a substrate on which the array is deposited, although the unit may include other features (such as a housing with a chamber). A "chamber" references an enclosed volume (although a chamber may be accessible through one or more ports). It will also be appreciated that throughout the present application, that words such as "top", "upper", and "lower" are used in a relative sense only. Wavelengths are peak wavelengths unless otherwise indicated.

A "same waveband" in relation to the light illuminating the array means having a spectral peak at the same wavelength, plus or minus 20 nm (and can include the same plus or minus 10, 5 or 1 nm). In an array reader which reads the array in different wavebands (for example, different color channels) any band overlap is best minimized by using light sources with narrow half-height peak emission spectra (for example, no more than 20, 10, or 5 nm) such as provided by different color lasers of half-height emission width typically smaller than 0.1 nm. However, for or emission of fluorescent dyes or phosphors the half-height width may be wider. Wavelengths are measured in a gas (such as air or nitrogen), or a vacuum, whichever one is in contact with the array during reading, unless the contrary is indicated.

By light "intensity" is referenced photon flux per unit area (that is, the number of photons per unit area per unit time, such as photons/second/m$^2$).

A "processor" references any hardware and/or software combination which will perform the functions required of it. For example, any processor herein may be a programmable digital microprocessor such as available in the form of a mainframe, server, or personal computer (desktop or portable). Where the processor is programmable, suitable programming can be communicated from a remote location to the processor, or previously saved in a computer program product (such as a portable or fixed computer readable storage medium, whether magnetic, optical or solid state device based). For example, a magnetic or optical disk may carry the programming, and can be read by a suitable disk reader communicating with each processor at its corresponding station. Reference to a singular item, includes the possibility that there are plural of the same items present. "May" means optionally. Methods recited herein may be carried out in any order of the recited events which is logically possible, as well as the recited order of events. All patents and other references cited in this application, are incorporated into this application by reference except insofar as they may conflict with those of the present application (in which case the present application prevails).

Figure 2:
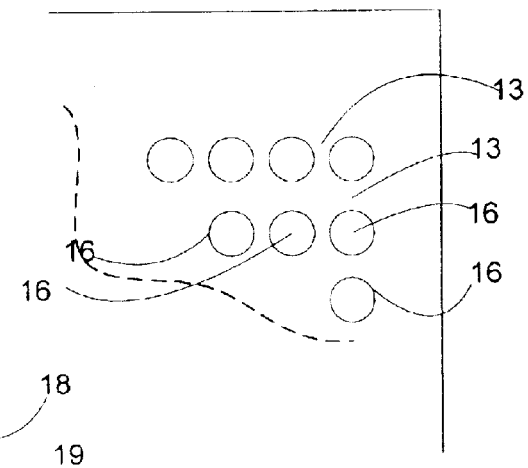
FIG. 2 is an enlarged view of a portion of FIG. 1 showing some of the identifiable individual features of a single array of FIG. 3.
Figure 3:
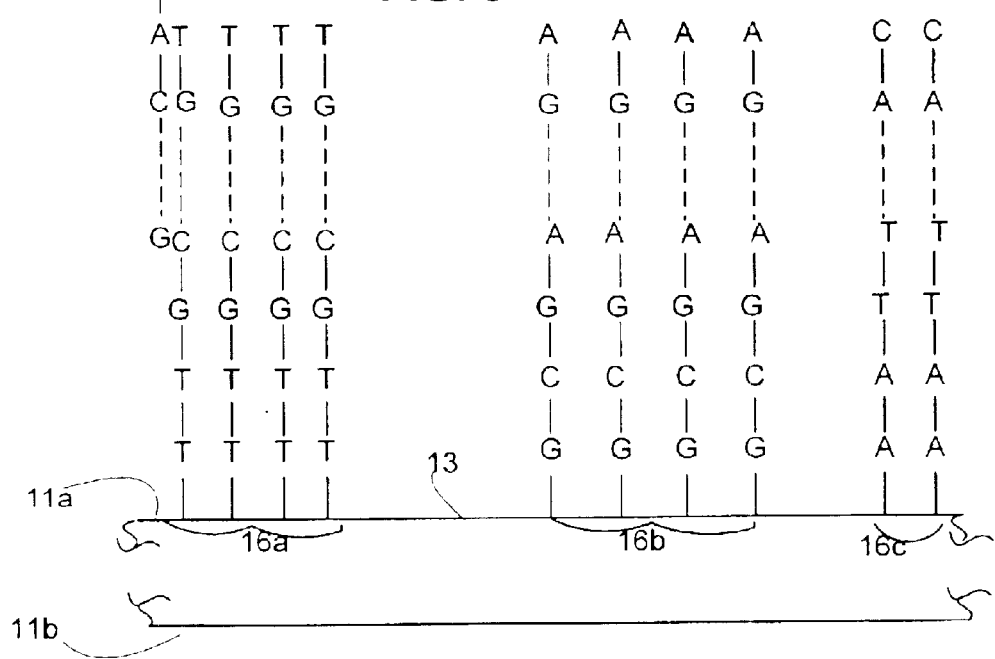
FIG. 3 is an enlarged cross-section of a portion of FIG. 2.

Referring now to FIGS. 1–3, an array unit 30 of the present invention includes a contiguous planar transparent substrate 10 carrying multiple features 16 disposed across a front surface 11a of substrate 10 and separated by interfeature areas 13. Features 16 are disposed in a pattern which defines the array. A second surface 11b of substrate 10 does not carry any features. Substrate 10 may be of any shape although the remainder of any unit carrying substrate 10, and the apparatus of the present invention, may need to be adapted accordingly. A typical array may contain at least ten features 16, or at least 100 features, at least 1,000, at least 100,000 features, or more. All of the features 16 may be of different composition, or some could be the same (for example, when any repeats of each feature composition are excluded the remaining features may account for at least 5%, 10%, 20%, or 50% of the total number of features). Each features carries probes in the form of a one moiety or mixture of moieties, which in the case of each feature 16 in FIGS. 1–3 is a polynucleotide having a particular sequence, while interfeature areas 13 do not carry any moieties of a type the same as the features 16 (for example, no polynucleotides in the case of features 16 carrying polynucleotides). This is illustrated schematically in FIG. 3 where regions 16 are shown as carrying different polynucleotide sequences. Features 16 may have widths (that is, diameter, for a round spot) of at least 5 or 10 $\mu$m, and less than 1.0 cm. In embodiments where very small spot sizes or feature sizes are desired, each of the features 16 may have widths of at least 1.0 $\mu$m and less than 1.0 mm, usually less than 500 $\mu$m, and more usually less than 200 $\mu$m. Features which are not round may have areas equivalent to the area ranges of round features 16 resulting from the foregoing diameter ranges.

The probes of features 16 are typically linked to substrate 10 through a suitable linker, not shown. Suitable materials for base substrate 10 include, for example, silica, glass, sapphire, or a plastic (that is, a synthetic or processed high molecular weight polymer that is, or is not, thermosetting or thermoplastic). Substrate 10 may have a thickness of at least 1 micrometer (or at least 5, 10 or 100 micrometers), or at least 1 mm. Substrate 10 may be transparent to the wavelength of the interrogating and detected emitted light. The front surface 11a of substrate 10 may be modified with one or more different layers of compounds that serve to modify the properties of the surface in a desirable manner. Front surface 11a should ideally exhibit a low level of binding during hybridization or other events.

The array 12 may cover an area of less than 100 cm$^2$, or even less than 50, 10 or 1 cm$^2$. In many embodiments, substrate 10 will be shaped generally as a rectangular solid (although other shapes are possible), having a length of more than 4 mm and less than 1 m, usually more than 4 mm and less than 600 mm, more usually less than 400 mm; a width of more than 4 mm and less than 1 m, usually less than 500 mm and more usually less than 400 mm; and a thickness of more than 0.01 mm and less than 5.0 mm, usually more than 0.1 mm and less than 2 mm and more usually more than 0.2 and less than 1 mm.

An array identifier 40 in the form of a machine readable bar code in FIG. 1, is associated with the array 12, by being provided on the same substrate 10 adjacent one of the arrays 12. Of course, codes other than a bar code could be used (for example, a solid state or magnetic memory carrying the identifier 40 could be provided). In the case where more than one array 12 is present on the same substrate 10, a separate identifier can be provided adjacent each corresponding array 12 if desired. Identifier 40 may either contain information on the layout of array 12 as well as any one or more of the following instructions or information, or be linkable to a file containing one or more of the following instructions or information in a manner such as described in U.S. Pat. No. 6,180,351: instructions that different regions of the array can be simultaneously illuminated with light of different intensities; that the light of the foregoing different intensities should be of the same waveband (and optionally originating from the same source, such as a laser); that light emitted from the different regions in response to the illuminating can be simultaneously detected from those regions with different detectors; an indication of the relative light intensities for the simultaneously illuminated regions or detector sensitivities for the simultaneously detected regions. Each identifier 40 for different arrays may be unique so that a given identifier will likely only correspond to one array 12 or to arrays 12 on the same substrate 10. This can be accomplished by making identifier 40 sufficiently long and incrementing or otherwise varying it for different arrays 12 or arrays 12 on the same substrate 10, or even by selecting it to be globally unique in a manner in which globally unique identifiers are selected as described in U.S. Pat. No. 6,180,351.

Arrays such as those of FIGS. 1–3 can be fabricated using drop deposition from pulse jets of either polynucleotide precursor units (such as monomers) in the case of in situ fabrication, or the previously obtained polynucleotide. Such methods are described in detail in, for example, the previously cited references including U.S. Pat. Nos. 6,242,266, 6,232,072, 6,180,351, 6,171,797, 6,323,043, U.S. patent application Ser. No. 09/302,898 filed Apr. 30, 1999 by Caren et al., and the references cited therein. As already mentioned, these references are incorporated herein by reference. Other drop deposition methods can be used for fabrication, as previously described herein. Also, instead of drop deposition methods, other array fabrication method may be used such as described in U.S. Pat. Nos. 5,599,695, 5,753,788, and 6,329,143. Interfeature areas 13 need not be present particularly when the arrays are made by light directed methods as described in those patents.

In use, the features 16 of array 12 are simultaneously exposed to a sample such as by contacting the different features 16 simultaneously with a layer of the same sample fluid, such that at least some of the features bind to respective moieties in the sample which sample moieties include the fluorescent label. For example, different polynucleotide sequences at respective features 16 can each hybridize to a complementary sequence, such as polynucleotides at feature 16a in FIG. 3 hybridizing to, and detecting, polynucleotide 18 from the sample. The "*" on polynucleotide 18 indicates a label 19, such as a fluorescent label, of a detected polynucleotide 18. Such labels 19 are the molecular sub-groups which act as locations which emit light in response to the interrogating light.

Figure 4:
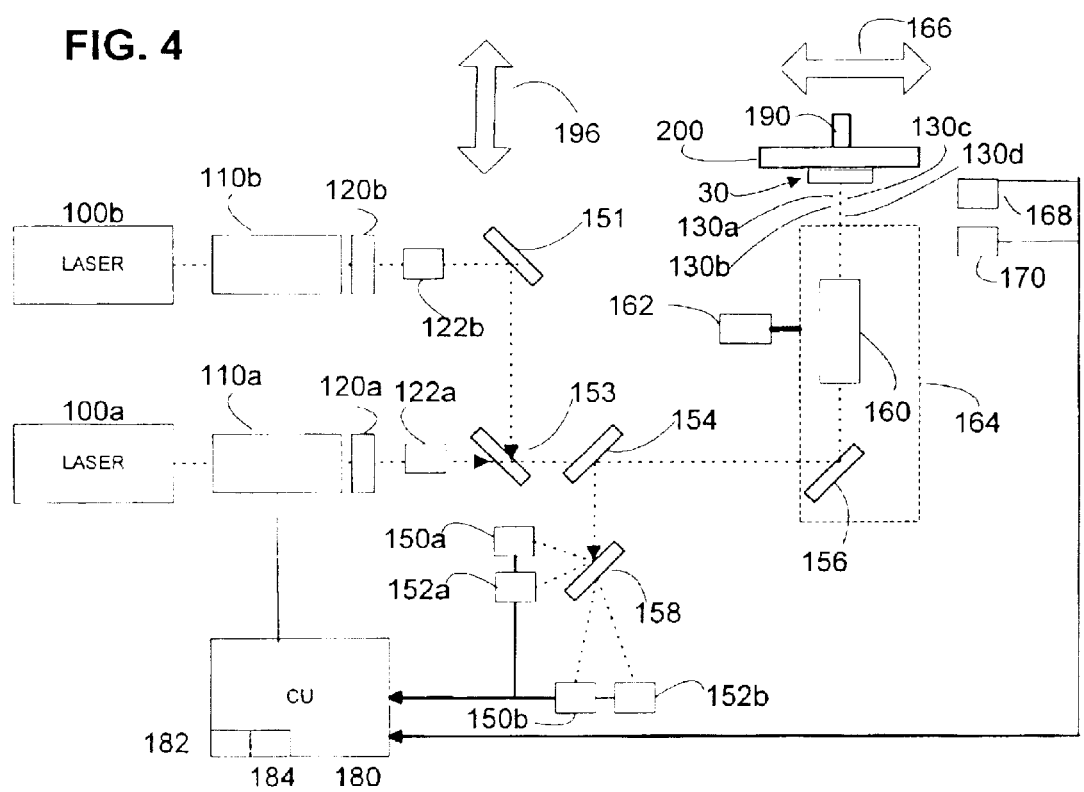
FIG. 4 schematically illustrates an apparatus of the present invention.
Figure 5:
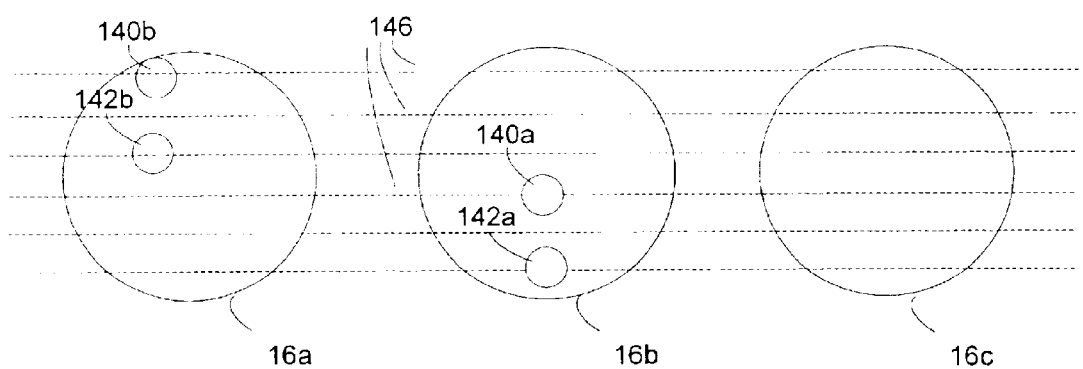
FIG. 5 illustrates the illumination of different regions of an array in the apparatus of FIG. 4, according to a method of the present invention.

Referring now to FIGS. 4 and 5, an apparatus of the present invention (which may be generally referenced as an array "scanner") and its operation according to a method of the present invention, are illustrated. A light system provides coherent light from a laser 100 which passes through an electro-optic modulator (EOM) 110 with attached polarizer 120. Each laser 100a, 100b may be of different wavelength (for example, laser 100a providing red light with a peak emission at 630 nm, and laser 100b providing green light with a peak emission at 530 nm) and each has its own corresponding EOM 110a, 110b and polarizer 120a, 120b. The resulting light beams are coherent and monochromatic. Beam splitter 122a splits the single beam from the same light source, namely laser 100a, into two beams at a small diverging angle to one another. The two beams are of the same waveband (and, since they originate from the same laser 100a, have the same spectral distribution) but of different light intensities. For example, they may have intensities relative to one another of at least 100/1, 50/1, 20/1, 10/1, or at least 5/1 or 2/1. Similarly, beam splitter 122b splits the single beam from the same light source, namely laser 100b, into two beams also at a small diverging angle to one another. The resulting two beams are of the same waveband as one another (although different from those from splitter 122a) and may have intensities relative to one another as already described in connection with those obtained from beam splitter 122a. Thus, there are a total of two pairs of interrogating light beams (two red of different intensities, and two green of different intensities). "Beam splitter" in the foregoing description in relation to beam splitters 122a, 122b, is used to include any configuration which will generate two beams of different intensity from one another from a same single source beam. Such devices may include diffractive elements such as a diffractive element that directs, for example, 1% of the beam intensity into a direction different from that of the main beam. Another beam splitter configuration which can generate two beams of different intensity from a single beam and at a small angle to one another, is a transparent wedge where the beam of highest intensity is the transmitted beam and the beam of lower intensity is reflected once at each surface. Polarizing beam splitters can also be used for this purpose, possibly in conjunction with EOMs or retardation plates. The beam splitter(s) used to generate spots of differing intensity can be located anywhere between the laser(s) and the array to be scanned. In particular, designs with a shared beam splitter for different wavelengths between dichroic splitter 153 and sample are conceivable, too.

The two interrogating beams of the red pair originating from laser 100a and beam splitter 122a are directed along respective paths 130a, 130b, while the two interrogating beams of the green pair originating from laser 100b and beam splitter 122b are directed along respective paths 130c, 130d. Light is directed along all of the paths 130a, 130b, 130c, 130d by means of full mirror 151, dichroic mirror 153, and full mirror 156 onto four different locations of an array being read (namely an array 12 of an array unit 30 mounted on holder 200), using optical components in beam focuser 160. Note though that FIG. 4 shows the paths 130a, 130b, 130c, 130d of these four beams as being coincident up until the position of a mirror 158, for the sake of simplicity. The angle of separation of the beams may be such that each interrogating light beam is directed along a corresponding path 130a, 130b, 130c, 130d toward front surface 11a at an angle equal that for example is greater than or equal to 0 degrees, to 45 degrees to a normal to the back surface (for example less than 1 degree, such as 0.5 degrees). Such an arrangement allows the four interrogating light beams to pass through the same optical system while reducing saturation of fluorescent labels at features 16 as well as channel cross-talk. A control signal in the form of a variable voltage applied to each corresponding EOM 110a, 110b by the controller (CU) 180, changes the polarization of the exiting light which is thus more or less attenuated by the corresponding polarizer 120a, 120b. Controller 180 may be or include a suitably programmed processor. Thus, each EOM 110 and corresponding polarizer 120 together act as a variable optical attenuator which can alter the power density of the light exiting from the attenuator. Hence each EOM 110 alters the power density of each interrogating light spot within a pair of light spots originating from the same laser. However, the relative power density of spots within a pair will remain the same (since beam splitters 122a, 122b are passive). Of course, entirely or partially separate optical components could be provided for each pair of interrogating light beams (or even for each of the four interrogating light beams) Similarly, entirely or partially separate optical components could be provided for light emitted and detected from each pair of the different regions in response to the illuminating (or even for each of the four different regions).

Each of the four beams provided on paths 130a, 130b, 130c, 130d then provide four spatially separated spots on an array 12 of an array unit 30 mounted on holder 200. These may be focused on front surface 11a directly without passing through substrate 10 when the array is being read with front surface 11a facing beam focuser 160 (that is, facing down in FIG. 4), or may be focused on front surface 11a after first passing through substrate 10 when the array is being read with front surface 11a facing away from beam focuser 160 (that is, facing up in FIG. 4). Various patterns for the spot separation can be used but the pattern of spots relative to one another will generally remain fixed unless independent optics were provided for the different beam paths 130. One such pattern is illustrate in FIG. 5. FIG. 5 illustrates a raster scan configuration in which each of the interrogating light spots is scanned along each line 146 (a transition of each spot from the current line to the next adjacent line, for example the next lower line in FIG. 5, occurring at the point which all of them have completed scanning their current line). In FIG. 5 red light of different intensities from beams 130a, 130b (both originating from the same laser 100a) simultaneously illuminate different regions in the form of spots 140a, 142a on different scan lines of one feature 16b, while green light of different intensities from beams 130c, 130d (both originating from the same laser 100b) simultaneously illuminate regions in the form of spots 140b, 142b on different scan lines of another feature 16a. If the beams are transitioning to the next lower line at the end of scanning a current line, it may be desirable that spots 142a and 142b are the lower intensity spots of each pair so that a given region on a feature is illuminated with the lower intensity light first to reduce the chance of triplet saturation at that region in a manner as described in U.S. Pat. No. 6,320,196. Note also that with the foregoing configuration the longer wavelength red light (at spots 140a, 142a) illuminate a given region of a feature before spots of the shorter green light (at 140b, 142b) also tending to reduce triplet saturation as again described in the foregoing patent. However, as already mentioned many other configurations of spots 140a, 140b, 142a, 142b could be used as desired.

Light emitted, in particular fluorescence, at two different wavelengths (for example, green and red light) from regions illuminated by spots 140a, 142a, 140b, 142b, in response to the interrogating light, is imaged using the same optics in focuser/scanner 160, and is reflected off mirrors 156 and 154. The two different wavelengths are separated by a further dichroic mirror 158. There will be four paths of detection each separated by a small angle, resulting from the spaced interrogating light spots 140a, 142a, 140b, 142b. As already mentioned though, for the sake of clarity these are only shown as one path in FIG. 4 up until mirror 158. Dichroic mirror 158 will direct red fluorescent light resulting from spots 140a, 142a onto detectors 150a and 152a, respectively of a detector pair, while green fluorescent light resulting from spots 140b, 142b will be directed onto detectors 150b, 152b, respectively, of another pair. More optical components (not shown) may be used between the dichroic and each of the four detector 150, 152 (such as lenses, pinholes, filters, fibers etc.) and each detector 150, 152 may be of various different types (e.g. a photo-multiplier tube (PMT) or a CCD or an avalanche photodiode (APD)). All of the optical components through which light emitted from an array 12 in response to the illuminating laser light, passes to the four detectors 150, 150, together with those detectors, form a detection system. This detection system has a fixed focal plane on the array 12 being read.

Instead of using dichroic 158, one can also use a design that images the different scanning spots onto different light-guiding fibers that then guide the signal from each one of these to a different detector. Such an arrangement for two scanning spots is described in U.S. Pat. No. 6,320,196.

The detectors 150a, 152a are set with the same sensitivities to one another, as are detectors 150b, 152b. However, some variation in sensitivities is acceptable although typically any sensitivity difference should be less than the excitation intensities, so that one obtains different "overall" sensitivities from the two detectors of a pair for the same waveband. In the foregoing, "overall sensitivity" is the product of illumination power and detector sensitivity. Similarly, detector 150b which detects green fluorescent light from the region of more intensely illuminated spot 140b will be set to the same or somewhat varied sensitivities as discussed above in connection with detectors 150a, 152a. This then allows for simultaneously detecting with the same or somewhat varied sensitivity detectors 150a, 152a, light emitted from the different regions 140a, 142a in response to the simultaneous illuminating with light of different intensities of the same waveband. This is similarly true for detectors 152b, 150b and spots 142b, 140b, respectively.

In order to raster scan spots 140a, 142a, and 140b, 142b in the manner already described, the scanner is provided with a scan system. In this manner, each of the multiple features 16 of the array is read, with each read feature containing multiple pixels (for example, more than five, ten, or twenty). This can be accomplished by providing a housing 164 containing mirror 158 and focuser 160, which housing 164 can be moved in a first direction along a line (that is, from left to right or the reverse as viewed in FIG. 4) by a transporter 162. The second direction 192 of scanning (line transitioning) can be provided by second transporter which may include a motor and lead screw or belt (not shown) to move holder 200 along one or more tracks. The second transporter may use a same or different actuator components to accomplish coarse (a larger number of lines) movement and finer movement (a smaller number of lines). The reader of FIG. 4 may further include a machine reader which reads an identifier 40 from an array unit 30 and provides the read identifier to controller 180. When identifier 40 is in the form of a bar code, that reader may be a suitable bar code reader 168.

An autofocus detector 170 is also provided to sense any offset between different locations on array 12 when in the reading position, and a determined position of the focal plane of the detection system. An autofocus system includes detector 170, processor 180, and a motorized adjuster to move holder in the direction of arrow 196. A suitable chemical array autofocus system is described in pending U.S. patent application Ser. No. 09/415,184 for "Apparatus And Method For Autofocus" by Dorsel et al., filed Oct. 7, 1999, incorporated herein by reference, as well as European publication EP 1091229 published Apr. 11, 2001 under the same title and inventors.

Controller 180 of the apparatus is connected to receive signals from the detector pair 150a, 152a (these signals being one "channel"), while also receiving signals from detector pair 150b, 152b (forming another "channel"). The signals in each channel are obtained at each of the two detected wavelengths from emitted light for each scanned pixel on array 12 when at the reading position mounted in holder 200. Controller 180 also receives the signal from autofocus offset detector 170, and provides the control signal to EOM 110, and controls the scan system. Controller 180 may also analyze, store, and/or output data relating to emitted signals received from detectors 150a, 150b in a known manner. The controller 180 may optionally set any one or more of the following: the light intensities for the simultaneously illuminated spots 140a, 142a (by controlling EOM 122a); the light intensities of the simultaneously illuminated spots 140b, 142b (by controlling EOM 122b); and the sensitivities of one or more of the four detectors. This setting can be made in response to instructions which may include an indication of the light intensities for the simultaneously illuminated regions of a same waveband or detector sensitivities for the simultaneously detected regions. Such instructions may be carried in identifier 40 read by bar code reader 168, or the read code may be linked to a file containing such instructions which are either located in a local or remote memory (for example, in a manner the same as which various items of array information can be obtained using a bar code, as described in U.S. Pat. No. 6,180,351). In the case of a code linked to a file such as may be located in a remote memory, the code may be received and the instructions linked to that code retrieved from memory based on the code and then communicated back to the location from which the code was received. Note that in the apparatus of FIG. 4 controller 180 can only control the absolute values of the red light intensities (or the same for the green light interrogating light intensities). The relative light intensity of spots 140a, 142a with respect to one another, as well as the relative light intensity of spots 140b, 142b with respect to one another, is fixed by the properties of the hardware (specifically, beam splitters 122a, 122b). However, if different optical paths were provided for the beams exiting the beam splitters 122a, 122b (for example, by providing an EOM for each of the four resulting beams), the relative intensities of spots 140a, 142a in the red color channel could be varied (as could those for spots 140b, 142b within the green color channel).

Controller 180 may include a computer in the form of a programmable digital processor, and include a media reader 182 which can read a portable removable media (such as a magnetic or optical disk), and a communication module 184 which can communicate over a communication channel (such as a network, for example the internet or a telephone network) with a remote site (such as a database at which information relating to array unit 30 may be stored in association with the identifier 40). Controller 180 is suitably programmed to execute all of the steps required by it during operation of the apparatus, as discussed further below. Alternatively, controller 180 may be any hardware or hardware/software combination which can execute those steps.

In one mode of operation, the array in unit 30 is typically first exposed to a liquid aqueous sample (for example, placed directly on substrate 10). The array may then be washed with buffer then water, and dried following washing then inserted into a scanner for reading. Drying may be accomplished using any suitable drying method and conditions which will not decompose the probes and their bound targets, such as any suitable one or more of: air drying at room temperature or raised temperature; reduced pressure; centrifuging; or exposure to a dry unreactive gas stream (such as dry nitrogen). Following a given array unit 30 being mounted in the apparatus, the identifier reader may automatically (or upon operator command) read array identifier 40, and use this to retrieve information on the array layout as well as any further instruction as to how the array should be interrogated or read (for example, the intensities of different interrogating lights or the sensitivities of different detectors, as described above). As already mentioned, such information may be retrieved directly from the contents of identifier 40 when identifier 40 contains such information, with the retrieved information being based wholly or only in part upon the read identifier 40. Alternatively, identifier 40 may be used to retrieve such information from a database containing the identifier in association with such information. Such a database may be a local database accessible by controller 180 such as may be contained in a portable storage medium in drive 182 which is associated with package 30, such as by physical association with package 30 when received by the user (for example, by being in the same package), or by a suitable identification. Alternatively, the database may be a remote database accessible by controller 180 through communication module 184 and a suitable communication channel (not shown). The retrieved instruction on how the array should be interrogated and read, can be used by controller 180 to control or check any one or more of: light intensity for each interrogating light spot on the array; detector sensitivity for each light spot region on the array; and oriented of the array within the reader (for example, if the array 12 is facing toward focuser 160 (when the array is to be illuminated and read without light passing through the substrate) or away from it (for illuminating and reading the array through the substrate). Assuming that lasers 100a, 100b are already operating, controller 180 then operates EOMs 110a, 110b and detectors 150a, 152a, 150b, 152b so that each detector generates a signal from a corresponding one of the spots as it is raster scanned over the array 12, in the manner already described. Signals read from the two detectors within a channel can be combined into one file for that channel by controller 180, for subsequent display or further processing.

In apparatus and methods of the present invention, use of two interrogated regions of the same waveband but different intensities to obtain a high total dynamic range, allows the use of simple optical elements to split an interrogating light source beam. This can be advantageous over illuminating only one region in each color channel and trying to split the detected emitted light in some proportion in each channels with a beam splitter. This is so since it is generally more difficult to construct an optical system which will split a beam to a desired ratio of intensities as the spectral width (for example, the width of the ½ maximum peak height) increases, and the emitted fluorescent light tends to have such a higher spectral width than an interrogating laser light. This difficulty can be further exacerbated by the fact that different end users might use different fluorescent labels in a same waveband, which different labels have different emission spectra. Thus, desired beam splitting ratios are easier to obtain for laser light than for the fluorescence the former excites.

The saved results from a sample exposed array, read according to a method of the present invention, may be raw results (such as fluorescence intensity readings for each feature in one or more color channels) or may be processed results such as obtained by rejecting a reading for a feature which is below a predetermined threshold and/or forming conclusions based on the pattern read from the array (such as whether or not a particular target sequence may have been present in the sample or whether an organism from which the sample was obtained exhibits a particular condition). The results of the reading (processed or not) may be forwarded (such as by communication of data representing the results) to a remote location if desired, and received there for further use (such as further processing).

It will be appreciated that various modifications can be made to the present invention. For example, a variety of geometries of the features 16 may be constructed other than the organized rows and columns of the array of FIGS. 1–3. For example, features 16 can be arranged in a series of curvilinear rows across the substrate surface (for example, a series of concentric circles or semi-circles of spots), and the like. Even irregular arrangements of features 16 can be used, at least when some means is provided such that during their use the locations of features of particular characteristics can be determined (for example, a map of the features is provided to the end user with the array). Furthermore, substrate 10 could carry more than one array 12, arranged in any desired configuration on substrate 10. While substrate 10 is planar and rectangular in form, other shapes (for example, circular) could be used with housing 34 being adjusted accordingly. In many embodiments, substrate 10 will be shaped generally as a planar, rectangular solid, having a length in the range about 4 mm to 200 mm, usually about 4 mm to 150 mm, more usually about 4 mm to 125 mm; a width in the range about 4 mm to 200 mm, usually about 4 mm to 120 mm and more usually about 4 mm to 80 mm; and a thickness in the range about 0.01 mm to 5.0 mm, usually from about 0.1 mm to 2 mm and more usually from about 0.2 to 1 mm. However, larger substrates can be used. Less preferably, substrate 10 could have three-dimensional shape with irregularities in first surface 11a. In any event, the dimensions of housing 34 may be adjusted accordingly. Additionally, during scanning it is possible to illuminate all pixels of a line simultaneously (for example, by using a line of light emitting diodes). In this case, two lines of different intensity could be used for each waveband (for example, two red lines of different intensity and two green lines of different intensity).

Other various modifications to the particular embodiments described above are, of course, possible. Accordingly, the present invention is not limited to the particular embodiments described in detail above.

What is claimed is:

1. A method of interrogating an addressable array having a plurality of different chemical features, the method comprising:
   (a) simultaneously illuminating different regions of the array with light of different intensities and a ratio of intensities of at least 10/1; and
   (b) simultaneously detecting with different detectors, light emitted from the different regions in response to the illuminating.

2. A method of interrogating an addressable array having a plurality of different chemical features, the method comprising:
   (a) simultaneously illuminating different regions of the array with light of different intensities and of the same waveband; and
   (b) simultaneously detecting with different detectors, light emitted from the different regions in response to the illuminating;
       wherein the different regions are simultaneously illuminated with light of different intensities and of a same waveband.

3. A method according to claim 1 wherein the simultaneously detected light from the different regions are of a same waveband.

4. A method according to claim 1 wherein the different regions are simultaneously illuminated with light of different intensities and of a same waveband, and wherein the simultaneously detected light form the different regions are of a same waveband.

5. A method according to claim 3 wherein the different regions are simultaneously illuminated with light of different intensities and the same waveband which originate from a same light source.

6. A method according to claim 3 wherein the different regions are simultaneously illuminated with light of different intensities and the same waveband which originate from a same laser.

7. A method according to claim 1 wherein the chemical features comprise polynucleotides of different sequence.

8. A method according to claim 1 wherein the chemical features comprise peptides of different sequence.

9. A method according to claim 1 wherein different regions of the array are simultaneously illuminated with light of different intensities and the same wavelength by light beams which are scanned across the array.

10. A method according to claim 9 wherein the scanning is a raster scan.

11. A method according to claim 10 wherein the different regions of the array that are illuminated with light of different intensities and the same wavelength, are on different rows in the raster scan.

12. A method according to claim 1 wherein at least some of the features include a fluorescent label and the detected emitted light is fluorescence from the label.

13. A method according to claim 12 wherein the features include corresponding moieties linked to the substrate, the method additionally comprising, prior to illuminating the features, exposing the features to a sample such that at least some of the features bind to respective moieties in the sample which sample moieties include the fluorescent label.

14. A method comprising forwarding data representing a result of an interrogation obtained by the method of claim 1.

15. A method according to claim 14 wherein the data is communicated to a remote location.

16. A method comprising receiving data representing a result of an interrogation obtained by a method of claim 1.

17. A method according to claim 1 additionally comprising retrieving an instruction associated with the array and, based on the read instructions, setting intensities of the light which illuminates the different regions of the array or setting sensitivities of the detectors.

18. A method according to claim 17 wherein the instruction is retrieved from a memory based on a code on a substrate carrying the array or on an element which carries the substrate.

19. A method according to claim 1 wherein the relative intensities of the light illuminating the different regions is at least 5/1.

20. A method according to claim 19 wherein the relative intensities of the light illuminating the different regions is at least 10/1.

21. An apparatus for interrogating an addressable array having a plurality of different chemical features, the apparatus comprising:
   (a) a light system which simultaneously illuminates different regions of the array with light of different intensities and a ratio of intensities of at least 5/1; and
   (b) different light detectors which simultaneously detect light emitted from the different regions in response to the illuminating by the light system.

22. An apparatus for interrogating an addressable array having a plurality of different chemical features, the apparatus comprising:
   (a) a light system which simultaneously illuminates different regions of the array with light of different intensities and of the same waveband; and
   (b) different light detectors which simultaneously detect light emitted from the different regions in response to the illuminating by the light system.

23. An apparatus according to claim 21 wherein the light detectors simultaneously detect light from the different regions which is of a same waveband.

24. An apparatus according to claim 21 wherein the light system simultaneously illuminates the different regions with light of different intensities and of a same waveband, and wherein the detectors simultaneously detect light form the different regions which is of a same waveband.

25. An apparatus according to claim 24 wherein the light system provides the light of different intensities and the same waveband from a same light source.

26. An addressable array unit comprising:

an addressable array having a plurality of different chemical features:

either: (i) instructions that different regions of the array can be simultaneously illuminated with light of different intensities and that light emitted from the different regions in response to the illuminating can be simultaneously detected with different detectors, the instructions including an indication of the light intensities for the simultaneously illuminated regions or detector sensitivities for the simultaneously detected regions; or (ii) a machine readable code linked to such instructions.

27. An addressable array unit according to claim 26 wherein the addressable array unit includes the machine readable code on a substrate carrying the array or an element which carries the substrate.

28. A method comprising receiving the code from an array unit according to claim 26 and communicating the instructions in response to the received code.

* * * * *